United States Patent [19]
Das

[11] Patent Number: 5,823,832
[45] Date of Patent: Oct. 20, 1998

[54] ELECTRICAL CONNECTOR FOR USE WITH AN ELECTROENCEPHALOGRAPH ELECTRODE

[75] Inventor: Mohan Das, Westbury, N.Y.

[73] Assignee: Netech Corporation, Hicksville, N.Y.

[21] Appl. No.: 780,054

[22] Filed: Dec. 23, 1996

[51] Int. Cl.$^6$ .................................................. H01R 4/52
[52] U.S. Cl. ........................................................... 439/817
[58] Field of Search .................................. 439/817, 818, 439/909

[56] References Cited

FOREIGN PATENT DOCUMENTS

| | | | |
|---|---|---|---|
| 0382502 | 10/1932 | United Kingdom | 439/817 |
| 0604014 | 6/1948 | United Kingdom | 439/818 |

*Primary Examiner*—Neil Abrams
*Assistant Examiner*—Eugene G. Byrd
*Attorney, Agent, or Firm*—Hoffmann & Baron, LLP

[57] ABSTRACT

An electrical connector specifically structured for use with a cup-shaped electroencephalograph electrode includes a stationary inner stud and an outer shell mounted circumferentially about the inner stud and movable longitudinally and rotationally relative to the inner stud. The outer shell includes a top wall having stepped upper and lower surfaces which define a receiving pocket for receiving the cup-shaped electrode. The electrical connector further includes a compression spring for biasing the outer shell with respect to the inner stud to cause the inner stud and outer shell to exert a holding force on the cup-shaped electrode when the electrode is inserted into the receiving pocket.

13 Claims, 3 Drawing Sheets

ELECTRICAL CONNECTOR FOR USE WITH AN ELECTROENCEPHALOGRAPH ELECTRODE

BACKGROUND OF THE INVENTION

1. Field of the Invention

The present invention generally relates to electrical connectors, and more specifically relates to electrical connectors for medical instruments.

2. Description of the Prior Art

FIG. 1 illustrates a conventional and commonly used electrical lead 2 for an electroencephalograph (EEG). The electrical lead 2 includes a pin electrode 4 at one end, which is received by a mating female connector mounted on the electroencephalograph, and an EEG cup electrode 6, also commonly referred to as a "scalp" electrode, situated at the other end. The scalp electrode is affixed to the patient's head when an electroencephalogram is made.

As shown in greater detail in FIGS. 2 and 3, the scalp electrode 6 which is commonly used in practice today is cup-shaped overall, and includes a concave main body portion 8 with sidewalls 10 that converge from a major opening 12 to a smaller central opening 14, and may have a peripheral flange 16 extending radially and planarly from the concave body portion 8 at its widest point opposite from the smaller opening 14. The main body portion 8 further includes a boss 18 which extends laterally from the outside surface of the main body portion and which is used to connect the scalp electrode to the electrical lead 2.

An EEG simulator (not shown) is often used not only to test the continuity of the electrodes and the lead, but also, of course, to test the proper operation of the EEG. The simulator, such as the MiniSim (TM) patient simulator Catalog No. 330 manufactured by Netech Corporation of Hicksville, N.Y., generates a plurality of selectable waveform signals, simulating the signals received from a patient undergoing electroencephalography. The signals are provided to the EEG through the electrical leads connected to it. There may be as many as 50 electrical leads 2 with scalp electrodes 6 connected to the EEG, and there may be several EEG simulators used, providing various waveform signals to the EEG through the previously described electrical leads having scalp electrodes.

One of the problems encountered in the medical industry in using EEG simulators with EEG's and testing the continuity of the various electrical leads is the attachment of the leads to the simulator. As mentioned previously, the pin electrode 4 of the electrical lead is plugged into the mating connector on the EEG. The scalp electrode 6, however, is often held manually in place against the output signal contacts of the EEG simulator. This is not only cumbersome, especially when as many as 50 electrical leads may be required to be held in place against the simulator contacts, but also oftentimes results in improper testing of the EEG and its associated electrical leads, as there is no assurance that proper, low resistance contact with the output signal contacts of the EEG simulator is made.

OBJECTS AND SUMMARY OF THE INVENTION

It is an object of the present invention to provide an electrical connector for use with an electroencephalograph electrode.

It is another object of the present invention to provide an electrical connector which is structured to mate cooperatingly with an electroencephalograph cup or scalp electrode.

It is a further object of the present invention to provide an electrical connector for mounting on an electroencephalograph simulator and for receiving an electroencephalograph electrode and firmly selectively engaging the electrode.

It is yet another object of the present invention to provide an electrical connector which is structured to engage an electroencephalograph cup or scalp electrode and to provide a low resistance path through the connector to the electrode.

It is still a further object of the present invention to provide an electrical connector for an electroencephalograph electrode which is structured to facilitate engagement and disengagement of the electrode from the connector.

It is another object of the present invention to provide a disposable electrical connector which is structured to mate with a cup-shaped EEG electrode and which may be removably mounted on the skin of a patient.

In accordance with one form of the present invention, an electrical connector structured to mate with a cup-shaped EEG electrode includes a stationary inner stud. The inner stud includes, in one form, a threaded end which may receive a threaded nut for mounting the stud on a supporting structure, such as a printed circuit board or the housing of an electrical device, such as an EEG simulator.

The electrical connector further includes an outer shell which is mounted circumferentially about the inner stud and movable longitudinally and rotationally relative to the inner stud. The outer shell includes structure which defines a receiving pocket for receiving the cup-shaped EEG electrode.

The electrical connector further includes a biasing device, such as a compression string, for longitudinally biasing the outer shell with respect to the inner stud and thereby causing the inner stud and outer shell to exert a holding force on the cup-shaped electrode when the electrode is inserted into the receiving pocket.

In another form of the present invention, the electrical connector includes a stationary inner stud, a movable outer shell, and a biasing device, such as a compression spring, as mentioned previously, but the mounting structure for the electrical connector allows the connector to be removably mounted to the skin of a patient. The mounting means includes a flexible membrane on which the inner stud is mounted. A side wall extends from the flexible membrane and includes an adhesive surface for removably mounting the electrical connector to the skin of a patient. The side wall is preferably continuous about the periphery of the membrane and defines a central reservoir, which contains an electrically conductive substance, preferably a gel, which is in electrical communication with the inner stud and with the skin of the patient on which the electrical connector is mounted.

These and other objects, features, and advantages of this invention will become apparent from the following detailed description of illustrative embodiments thereof, which is to be read in connection with the accompanying drawing.

DETAILED DESCRIPTION OF THE PREFERRED EMBODIMENTS

Figure 1:
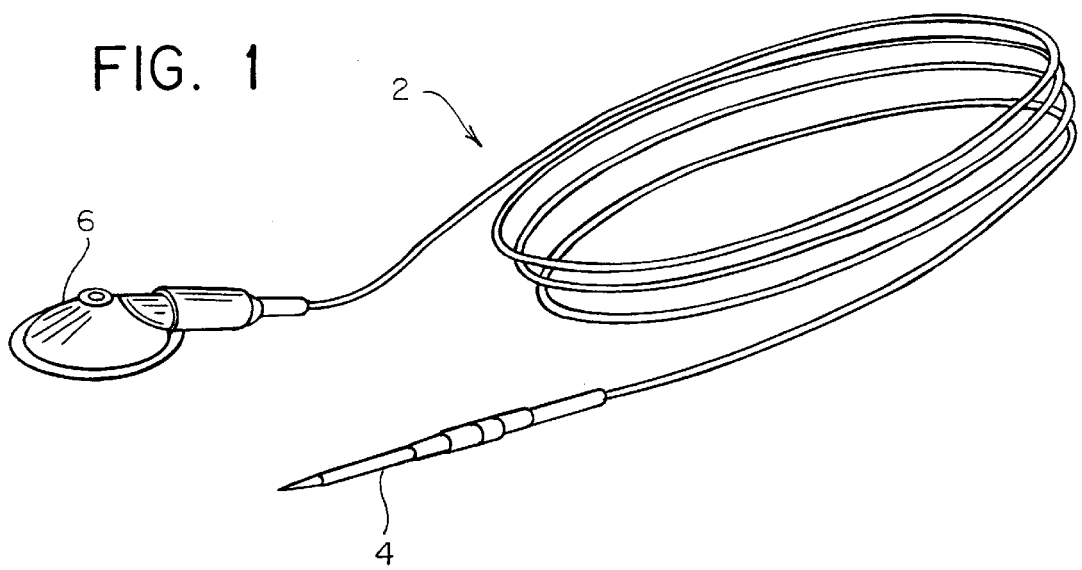
FIG. 1 is a perspective view of an electrical lead for use with an electroencephalograph (EEG), having on one end a cup-shaped "scalp" electrode and on the other end a pin electrode.
Figure 2:
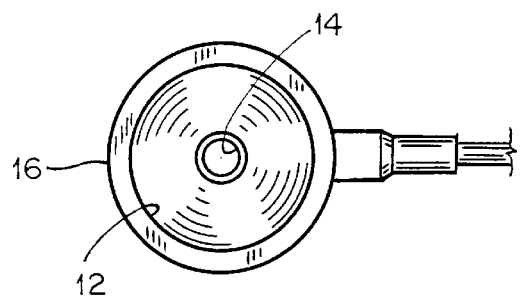
FIG. 2 is a side view of the cup-shaped electrode shown in FIG. 1.
Figure 4:
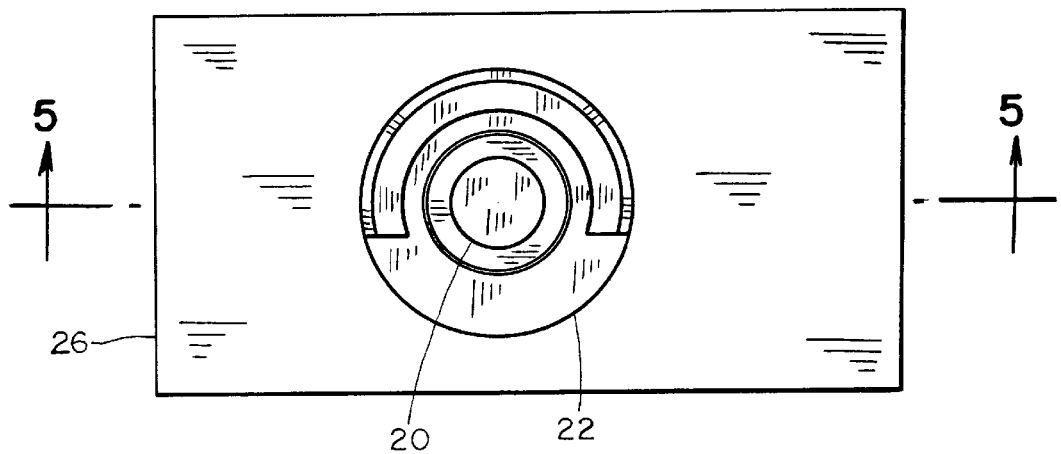
FIG. 4 is a top plan view of the electrical connector of the present invention.
Figure 5:
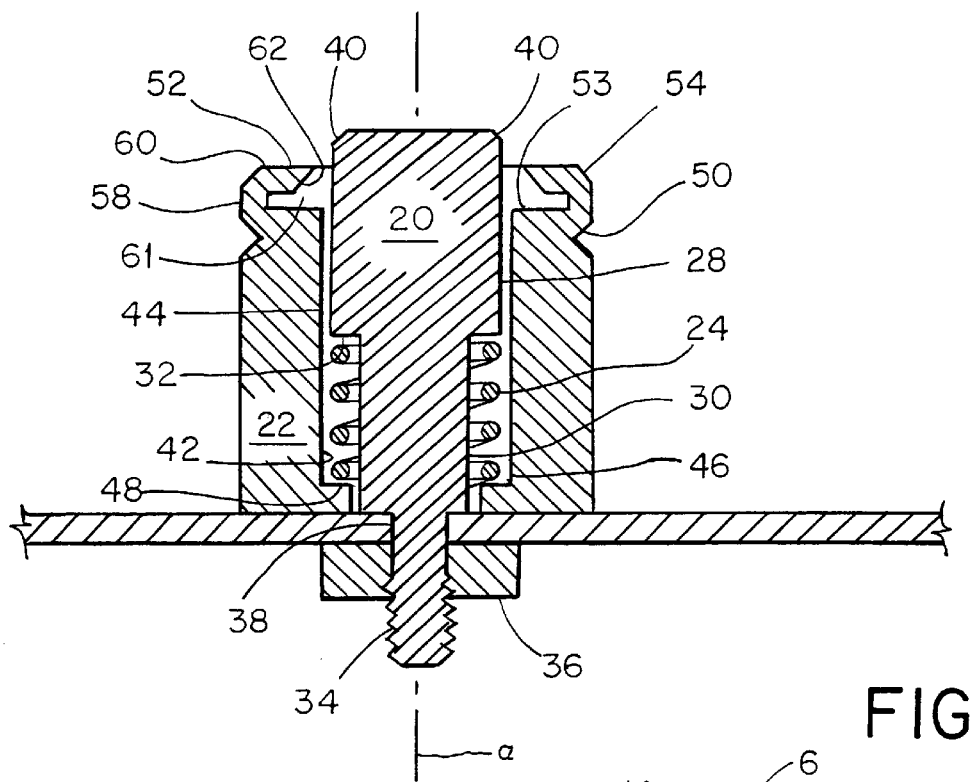
FIG. 5 is a cross-sectional view of the electrical connector of the present invention, taken along line 5—5 of FIG. 4.
Figure 3:
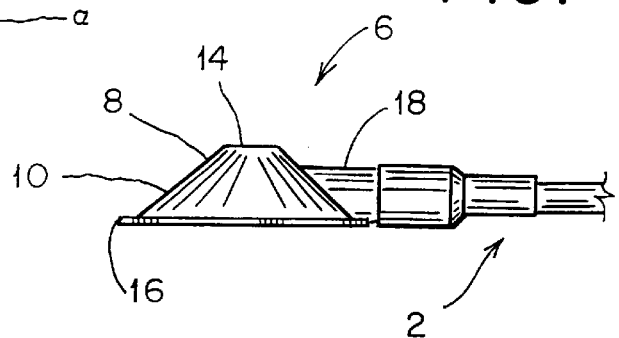
FIG. 3 is a bottom view of the cup-shaped electrode shown in FIGS. 1 and 2.

Referring initially to FIGS. 4 and 5 of the drawing, it will be seen that an electrical connector constructed in accordance with one form of the present invention, for receiving and mating with an EEG cup or "scalp" electrode 6 as described previously and shown in FIGS. 1–3, includes basically three components: an inner stud 20, an outer shell 22 and a biasing device, such as a compression spring 24.

The inner stud 20 is an elongate member residing along a longitudinal axis α, and preferably has a generally overall cylindrical shape. The inner stud 20 is stationary in that it is mounted to a printed circuit board or housing 26 of, for example, an EEG simulator, such as described previously, or other electrical device.

The inner stud 20 includes an enlarged diameter upper portion or head 28, and a shaft 30 mounted on the head 28 and extending therefrom along the longitudinal axis. The shaft 30 has a smaller diameter than that of the head 28 to define an upper shoulder 32 between the shaft 30 and the head 28 of the inner stud.

The inner stud 20 further has a lower portion 34 which is situated at one end of the shaft distally or opposite from the head. The lower portion 34 is preferably threaded to accept a threaded nut 36 so that the inner stud 20 and consequently the entire electrical connector may be mounted on the supporting structure 26, such as the PC board or the housing of the EEG simulator or other electrical device.

Even more preferably, the lower portion 34 of the inner stud, which is threaded, may have a smaller diameter than that of the rest of the shaft 30 to define a lower shoulder 38 between the threaded portion 34 and the rest of the shaft 30. The lower shoulder 38 is provided for contacting and resting on the supporting structure 26 to support the inner stud 20 in an upright or normal position with respect to the supporting structure, e.g., the printed circuit board or housing. Alternatively, the threaded portion 34 may have the same diameter as the rest of the shaft 30, and two threaded nuts (not shown) may be used for mounting the electrical connector to the printed circuit board or housing 26, with the printed circuit board or housing sandwiched between the two nuts.

Figure 6:
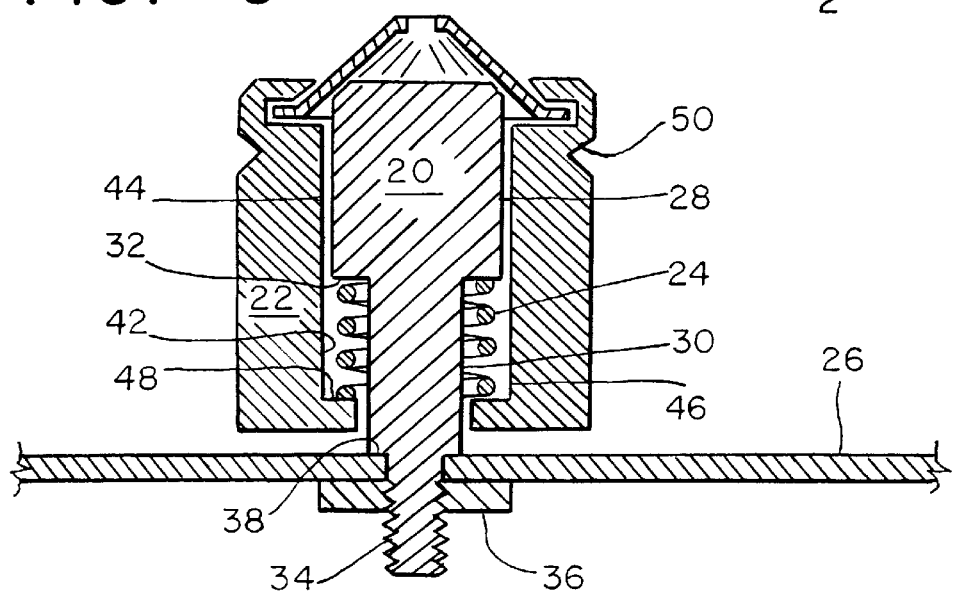
FIG. 6 is a longitudinal cross-sectional view of the electrical connector of the present invention shown mated with an EEG cup electrode.

The head 28 of the inner stud 20 is preferably formed with a beveled edge 40 about its upper periphery. The beveled edge 40 preferably has a slope (preferably, substantially 45° to the longitudinal axis of the stud) which conforms substantially to the slope of the side wall 10 of the EEG cup-shaped electrode 6 in order to rest against it when the EEG electrode is mated with the electrical connector, as shown in FIG. 6 of the drawing. This ensures greater surface area of the stud 20 in electrical contact with the cup electrode 6 and, consequently, a lower resistance electrical connection between the two.

The outer shell 22 is preferably cylindrical in shape and is disposed concentrically about and movably mounted on the inner stud 20. As will be seen, the outer shell 22 is rotationally and longitudinally movable relative to the stud 20. The outer shell 22 has a bore 42 extending longitudinally and centrally through it, from top to bottom. The bore 42 is defined by an upper inner side wall 44 and a lower inner side wall 46 extending from the upper inner side wall 44.

More specifically, the upper inner side wall 44 defines the upper portion of the bore 42, which has a diameter sufficient to receive, preferably closely to provide lateral support for the stud, the enlarged diameter head 28 of the inner stud. The lower portion of the bore 42 is defined by the lower inner side wall 46 and has a diameter which is sufficient to receive, again preferably closely, the shaft 30 of the inner stud. Thus, the upper inner side wall 44 has a diameter which is greater than that of the lower inner side wall 46 to define between the two a lower shoulder 48 and to attribute the outer shell with an overall "L" shape in longitudinal cross section. The inner stud 20 is received by the bore 42 of the outer shell 22, with the threaded portion 34 extending beyond the bottom of the outer shell.

The outer shell 22 has an outer surface with a recess 50 formed in it and extending circumferentially about the outer shell. The recess 50 is provided to facilitate grasping the outer shell 22 by a user for movement of the outer shell relative to the inner stud 20. Other grasping structure formed on the outer shell 22 is envisioned to be within the scope of the invention, such as a protruding ridge or ring (not shown) encircling the shell, or protruding tabs (not shown) mounted on the shell, for example.

The outer shell 22 further has a top wall with stepped upper and lower surfaces 52,53, respectively. The upper surface 52 includes an L-shaped portion 54 partially surrounding the peripheral edge of the top wall. For example, the L-shaped portion 54 may extend halfway about the periphery of the outer shell 22 or may extend further (i.e., greater than 180°) to form a side opening 56 having a width which is at least equal to that of the greatest diameter of the cup electrode 6 so that the cup electrode may be received through the side opening 56.

The L-shaped portion 54 of the top surface is formed with a first leg 58 extending substantially longitudinally from the lower surface 53 of the top wall, and a second leg 60 partially extending radially inwardly of the outer shell 22 from the first leg 58 so that the second leg 60 overlies at least a portion of the lower surface 53 of the top wall. This structure defines between the stepped upper surface and the lower surface of the top wall a receiving pocket 61 open on one side for receiving the cup-shaped electrode 6.

The L-shaped portion 54 of the upper surface 52 of the top wall may further have an inner wall 62 which slopes transversely to the longitudinal axis of the inner stud 20 (again, preferably at substantially 45°). The slope of the inner wall 62 of the L-shaped portion 54 substantially conforms to the side wall 10 of the cup electrode 6, and parallel to the beveled edge 40 of the inner stud 20, so that it rests against the sloping outer side wall 10 of the cup electrode when the electrode is mated with the electrical connector. Again, like the beveled edge 40 of the inner stud, the sloping inner wall 62 of the top wall of the outer shell 22 provides a greater surface area to engage the cup electrode 6 and provide a low resistance path between the two, although it is the inner stud 20 which is primarily relied on for providing the electrical connection with the electrode.

The biasing device, such as the compression spring 24 shown in FIG. 5 of the drawing, is mounted circumferentially about the shaft 30 of the inner stud 22 and engages the upper shoulder 32 of the inner stud and the lower shoulder 48 of the outer shell 22. The compression spring 24 biases the outer shell 22 and inner stud 20 in opposite directions along the same longitudinal axis α, thereby causing the inner stud and outer shell to engage and exert a holding force on the cup-shaped electrode 6 when the electrode is inserted into the receiving pocket 61 defined by the stepped upper and lower surfaces 52,53 of the outer shell.

With reference to FIG. 6 of the drawing, it will be seen that to connect the electrode 6 to the connector, the user grasps the outer shell 22 at the recess or groove 50 formed about its circumference and pulls upwardly away from the printed circuit board or housing 26, against the bias of the spring 24, until the top of the inner stud 20 is equal to or below the level of the stepped lower surface 53 of the top wall of the outer shell 22. This will effectively open the pocket for receiving the cup electrode 6.

When the cup electrode 6 is inserted through the side opening 56 and into the receiving pocket 61, the outer shell 22 is released by the user. The compression spring 24 biases the outer shell 22 downwardly relative to the inner stud 20 to wedge the cup electrode 6 between the outer shell and the inner stud, holding the cup electrode in place and forming a low resistance path between the inner stud 20 and the cup electrode 6.

Figure 7:
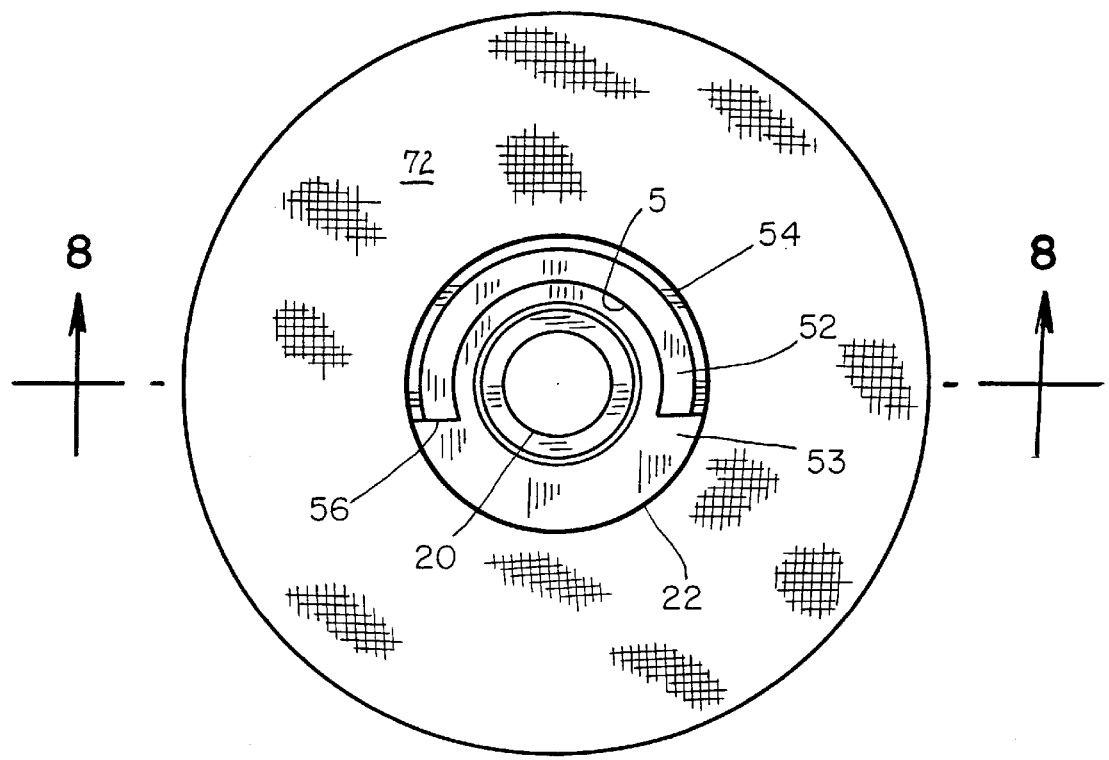
FIG. 7 is a top plan view of another embodiment of an electrical connector formed in accordance with the present invention.
Figure 8:
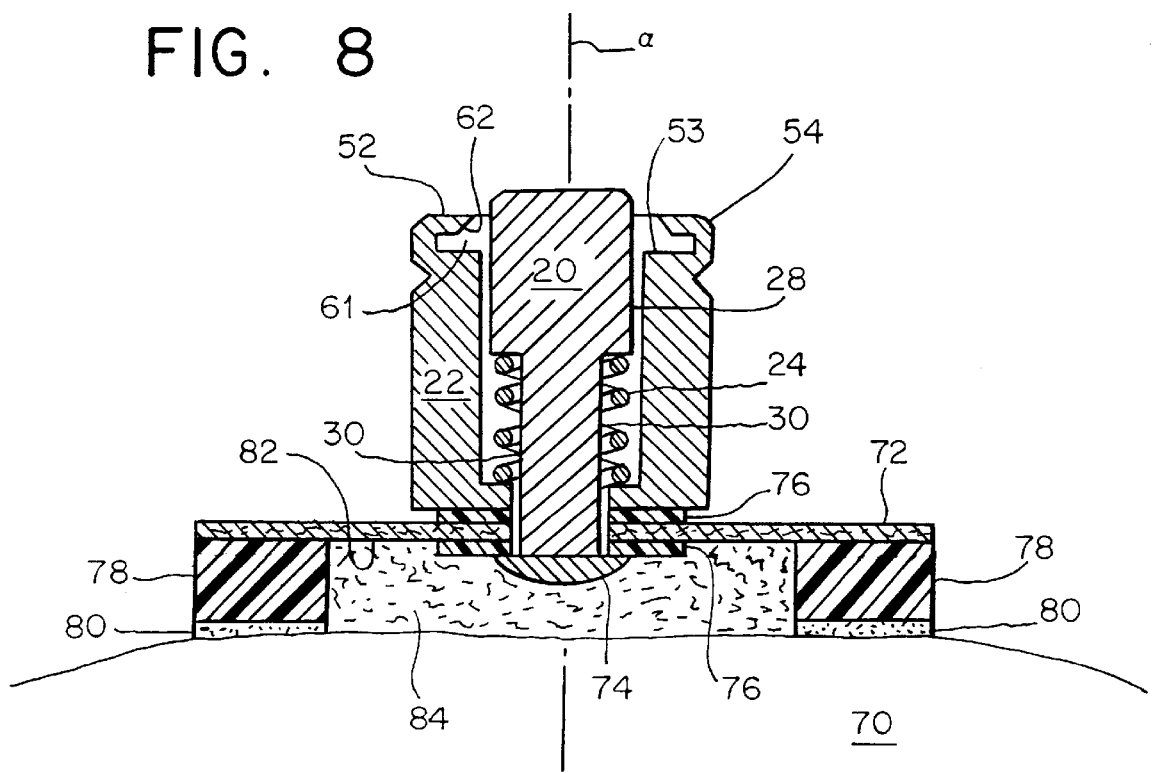
FIG. 8 is a cross-sectional view of the electrical connector shown in FIG. 7 taken along line 8—8 of FIG. 7 and shown removably attached to a patient.

FIGS. 7 and 8 of the drawing illustrate an alternative embodiment of the present invention, that is, a disposable electrical connector which mates with an EEG cup or "scalp" electrode 6 and which is attachable to and removable from the skin of a patient 70. As shown in FIGS. 7 and 8, the structure of the outer shell 22 and inner stud 20 remains substantially the same as that of the embodiment shown in FIGS. 4 and 5. However, the threaded portion 34 of the inner stud, which was used for mounting the electrical connector to a printed circuit board or housing 26 of an electrical device, is changed in this embodiment.

As shown in FIGS. 7 and 8, the structure for removably mounting the electrical connector to a patient 70 includes a flexible membrane 72, such as a cloth, tissue or foam. The flexible membrane 72 has opposite top and bottom surfaces. The inner stud 22 of the electrical connector has its lower portion ending in a rivet having of an enlarged button or head 74. Mounted on the lower portion of the shaft 30 of the inner stud 20 are two reinforcement washers 76. The shaft 30 of the inner stud passes through an opening in the flexible membrane 72, which membrane is sandwiched between the two reinforcement washers 76 so that the electrical connector is securely mounted to the flexible membrane 72 and disposed on the top surface of the membrane.

A side wall 78 is mounted on the flexible membrane 72 and extends from its bottom surface. The side wall 78 has an adhesive surface 80 for adhesion to and mounting of the electrical connector to the skin of a patient 70. The sidewall 78 is preferably continuous, traversing 360° about the longitudinal axis α of the inner stud, and defines a central reservoir 82 disposed on the bottom surface of the flexible membrane 72.

An electrically conductive substance 84, such as a conductive gel, is received by the central reservoir 82. Because the rivet or head 74 of the inner stud 20 projects into the reservoir 82 and forms part of the inner stud, the electrically conductive substance 84 in the central reservoir is in electrical communication with the inner stud 20 and, consequently, in electrical communication with the skin of a patient 70 when the electrical connector is mounted on the patient. Thus, a cup electrode 6 may be mated with the electrical connector of the present invention and be in electrical communication with the patient 70 rather than have the cup electrode being affixed directly to the patient, as is done conventionally. After use, the electrical connector may be removed from the patient and discarded.

Although the embodiment described above and shown in FIGS. 7 and 8 preferably employs a rivet 74 and reinforcement washers 76 to mount the electrical connector to the flexible membrane 72, it is envisioned that other fastening means may be employed which still provide electrical conductivity between the conductive gel 84 in the reservoir 82 and the inner stud 20. For example, the electrical connector shown in FIGS. 4 and 5 may be used. The flexible membrane 72 may be mounted on the threaded lower portion 34 of the inner stud, with the lower shoulder 38 of the stud resting on the top surface of the flexible membrane 72, and a nut 36 on the threaded portion tightened against the bottom surface of the flexible membrane. Alternatively, the upper washer 76 may be used to rest against the lower shoulder 38 of the inner stud, with the flexible membrane 72 sandwiched between it and the lower washer 76, and secured with a nut (not shown) tightened against the lower washer, or the flexible membrane 72 may be sandwiched between two nuts (not shown) mounted on the threaded portion 34 of the inner stud 22. In the examples described above, preferably a portion of the inner stud 20 or its associated mounting hardware at least partially resides in the reservoir 82 and contacts the conductive gel 84 received by the reservoir to provide a conductive path between the patient 70, the inner stud 20 and the cup electrode 6 held by the electrical connector. The present invention provides an electrical connector which is structured for use with cup-shaped electrodes, such as those used with electroencephalographs. The connector is easy to use by a physician or technician; the movable outer shell may easily be grasped and lifted on the stationary inner stud for insertion of the cup electrode, and forms a positive, low resistance connection between the cup electrode and the inner stud. The inner stud may be gold plated or plated with silver chloride to further reduce the resistance of the connection.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An electrical connector structured to mate with a cup-shaped electrode, which comprises:

a stationary inner stud having a longitudinal axis, the stationary inner stud including means for mounting the electrical connector to a supporting structure;

an outer shell mounted circumferentially about the inner stud and movable longitudinally and rotationally relative to the longitudinal axis of the inner stud, the outer shell including means defining a receiving pocket for receiving the cup-shaped electrode; and biasing means for longitudinally biasing the outer shell with respect to the longitudinal axis of the inner stud and thereby causing the inner stud and outer shell to exert a holding force on the cup-shaped electrode when the electrode is inserted into the receiving pocket.

2. An electrical connector as defined by claim 1, wherein the outer shell further includes means for facilitating grasping the outer shell to move the outer shell relative to the inner stud.

3. An electrical connector as defined by claim 2, wherein the outer shell includes an outer surface; and wherein the means for facilitating grasping the outer shell includes means defining a recess formed in the outer surface of the outer shell.

4. An electrical connector as defined by claim 1, wherein the outer shell includes a top wall; and wherein the means for defining a receiving pocket for the cup-shaped electrode includes stepped upper and lower surfaces formed in the top wall of the outer shell, the upper surface including an L-shaped portion partially surrounding the peripheral edge of the top wall of the outer shell and having one leg partially extending radially inwardly of the outer shell to overly at least a portion of the lower surface.

5. An electrical connector as defined by claim 4, wherein the radially inwardly extending leg of the L-shaped portion includes an inner wall sloping transversely to the longitudinal axis of the inner stud.

6. An electrical connector as defined by claim 5, wherein the inner stud includes an upper portion having a beveled edge, the slope of the beveled edge being substantially equal to the slope of the inner wall of the L-shaped portion of the outer shell so that the beveled edge and the inner wall extend in substantially parallel directions.

7. An electrical connector as defined by claim 6, wherein the slope of the beveled edge of the inner stud and the slope of the inner wall of the L-shaped portion of the outer shell are substantially 45° with respect to the longitudinal axis of the inner stud.

8. An electrical connector as defined by claim 2, wherein the means for biasing the outer shell with respect to the inner stud includes a compression spring.

9. An electrical connector as defined by claim 1, wherein the means for mounting the electrical connector to a supporting structure includes a threaded lower portion formed on the inner stud.

10. An electrical connector structured to mate with a cup-shaped electrode, the electrode including a concave main body portion having a sloping side wall, which comprises:

a cylindrical stationary inner stud having a longitudinal axis, the inner stud having an enlarged diameter upper portion and a shaft mounted on the upper portion and extending therefrom along the longitudinal axis, the shaft having a smaller diameter than that of the upper portion to define an upper shoulder therebetween, the inner stud further having a lower portion situated at one end of the shaft distally from the upper portion, the lower portion being threaded to accept a threaded nut and for mounting the inner stud to a supporting structure, the upper portion of the inner stud having a beveled edge, the edge having a slope which conforms substantially to the slope of the sloping side wall of the cup-shaped electrode and to rest thereagainst when the electrode is mated with the electrical connector;

a cylindrical outer shell disposed concentrically about and movably mounted on the inner stud rotationally and longitudinally relative to the longitudinal axis of the stud, the outer shell having an upper inner side wall and a lower inner side wall extending from the upper inner side wall, the upper and lower inner side walls respectively defining upper and lower portions of a bore extending longitudinally and centrally through the outer shell, the upper portion of the bore having a diameter sufficient to receive the enlarged diameter upper portion of the inner stud, the lower portion of the bore having a diameter sufficient to receive the shaft of the inner stud, the upper inner side wall having a diameter which is greater than that of the lower inner side wall to define therebetween a lower shoulder, the outer shell having an outer surface, the outer surface having a recess formed therein and extending circumferentially about the outer shell to facilitate grasping the outer shell for movement of the outer shell relative to the inner stud, the outer shell having a top wall with a peripheral edge, the top wall having stepped upper and lower surfaces, the upper surface including an L-shaped portion partially surrounding the peripheral edge of the top wall and being formed with a first leg extending substantially longitudinally from the lower surface and a second leg partially extending radially inwardly of the outer shell from the first leg to overlie at least a portion of the lower surface, thereby defining between the stepped upper surface and lower surface a receiving pocket open on one side thereof for receiving the cup-shaped electrode; and a compression spring, the compression spring being mounted circumferentially about the shaft of the inner stud and engaging the upper shoulder of the inner stud and the lower shoulder of the outer shell to longitudinally bias the outer shell with respect to the inner stud in a direction along the longitudinal axis thereof and to thereby cause the inner stud and outer shell to engage and exert a holding force on the cup-shaped electrode when the electrode is inserted into the receiving pocket.

11. An electrical connector as defined by claim 10, wherein the L-shaped portion of the upper surface has an inner wall sloping transversely to the longitudinal axis of the inner stud, the slope of the inner wall of the L-shaped portion substantially conforming to the slope of the sloping side wall of the cup-shaped electrode and to rest thereagainst when the electrode is mated with the electrical connector.

12. An electrical connector as defined by claim 10, wherein the lower portion of the inner stud has a smaller diameter than the diameter of the shaft of the inner stud to define a lower shoulder therebetween, the lower shoulder being provided for contacting the supporting structure and for supporting the inner stud normally to the supporting structure.

13. An electrical connector for removably mounting on the skin of a patient and structured to mate with a cup-shaped electrode, which comprises:

a stationary inner stud having a longitudinal axis;

an outer shell mounted circumferentially about the inner stud and movable longitudinally and rotationally relative to the longitudinal axis of the inner stud, the outer shell including means defining a receiving pocket for receiving the cup-shaped electrode;

biasing means for longitudinally biasing the outer shell with respect to the longitudinal axis of the inner stud and thereby causing the inner stud and outer shell to exert a holding force on the cup-shaped electrode when the electrode is inserted into the receiving pocket; and means for mounting the electrical connector to a patient, the mounting means including:

a flexible membrane, the flexible membrane having a top surface and a bottom surface disposed opposite to the top surface, the inner stud being mounted on the flexible membrane and disposed on the top surface thereof;

a side wall mounted on the flexible membrane and extending from the bottom surface thereof, the side wall having an adhesive surface for adhesion to and mounting of the electrical connector to the skin of a patient, the side wall defining a central reservoir disposed on the bottom surface of the flexible membrane; and an electrically conductive substance received by the central reservoir, the electrically conductive substance being in electrical communication with the inner stud and in electrical communication with the skin of a patient when the electrical connector is mounted thereon.

* * * * *